United States Patent [19]
Pike

[11] Patent Number: 5,967,490
[45] Date of Patent: Oct. 19, 1999

[54] CATHETER HUBS HAVING A VALVE

[75] Inventor: Kevin H. Pike, Clinton, Mich.

[73] Assignee: Vadus, Inc., Amesbury, Mass.

[21] Appl. No.: 08/898,605

[22] Filed: Jul. 22, 1997

Related U.S. Application Data

[63] Continuation-in-part of application No. 08/780,203, Jan. 8, 1997, abandoned.

[51] Int. Cl.⁶ .............................. F16L 29/00; A61M 5/00
[52] U.S. Cl. ........................ 251/149.1; 604/249; 604/256
[58] Field of Search ............................. 251/149.1, 149.4; 604/256, 167, 249, 283

[56] References Cited

U.S. PATENT DOCUMENTS 5,535,785  7/1996  Werge et al. ..................... 604/249 X
5,749,861  5/1998  Guala et al. ..................... 604/256 X

*Primary Examiner*—Kevin Lee
*Attorney, Agent, or Firm*—Gardner, Carton & Douglas

[57] ABSTRACT

A catheter hub including a housing having a connection end defining a first fluid passageway and a catheter end defining a second fluid passageway. The housing includes a plurality of hub walls arranged in a geometric configuration. The hub walls define a valve chamber. The catheter hub further includes a valve positioned in the valve chamber for controlling fluid flow through the chamber between the first and second fluid passageways. The catheter hub further includes an actuator for actuating the valve. The catheter hub regulates fluid flow between the first and second fluid passageways.

19 Claims, 7 Drawing Sheets

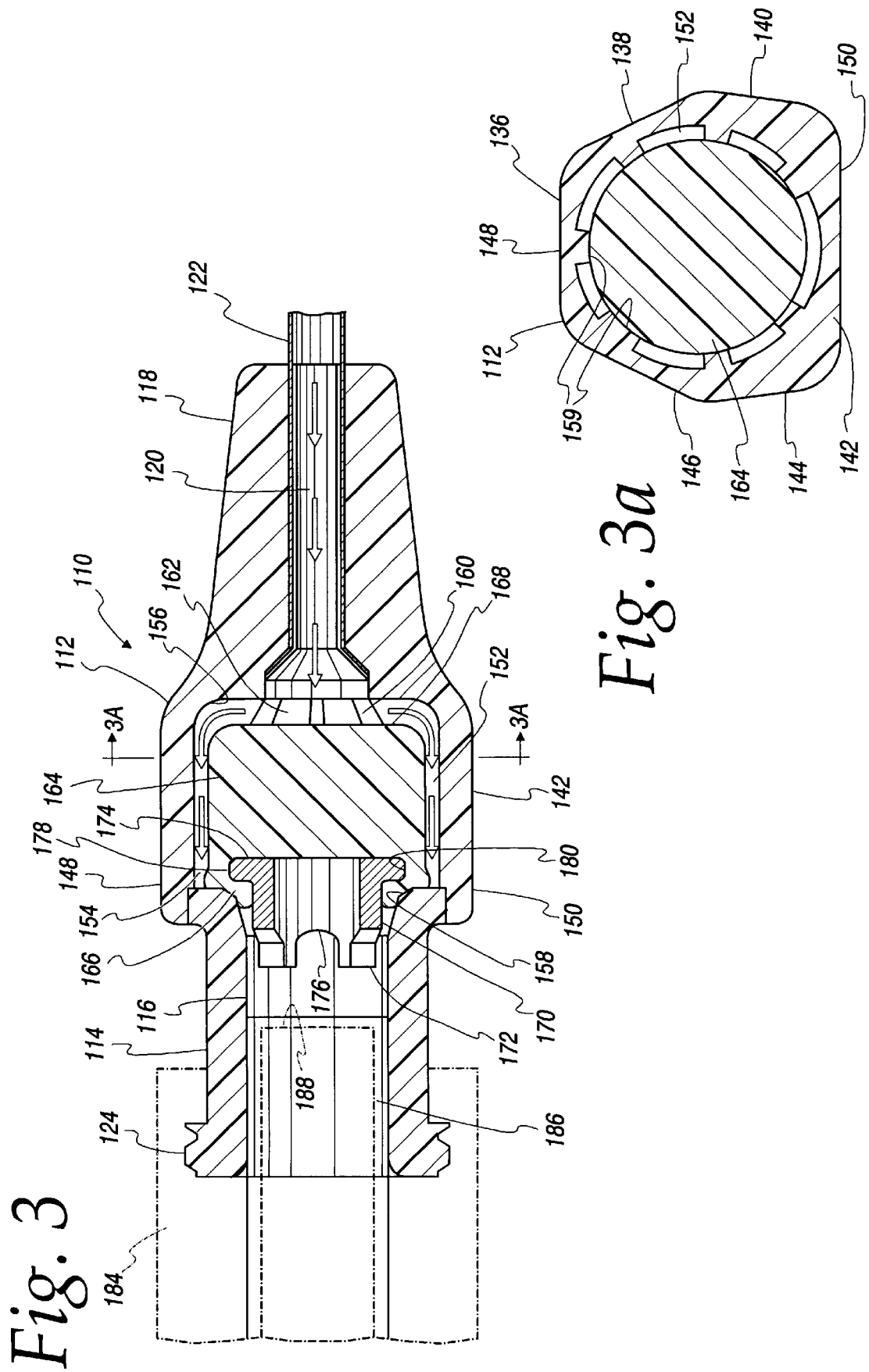

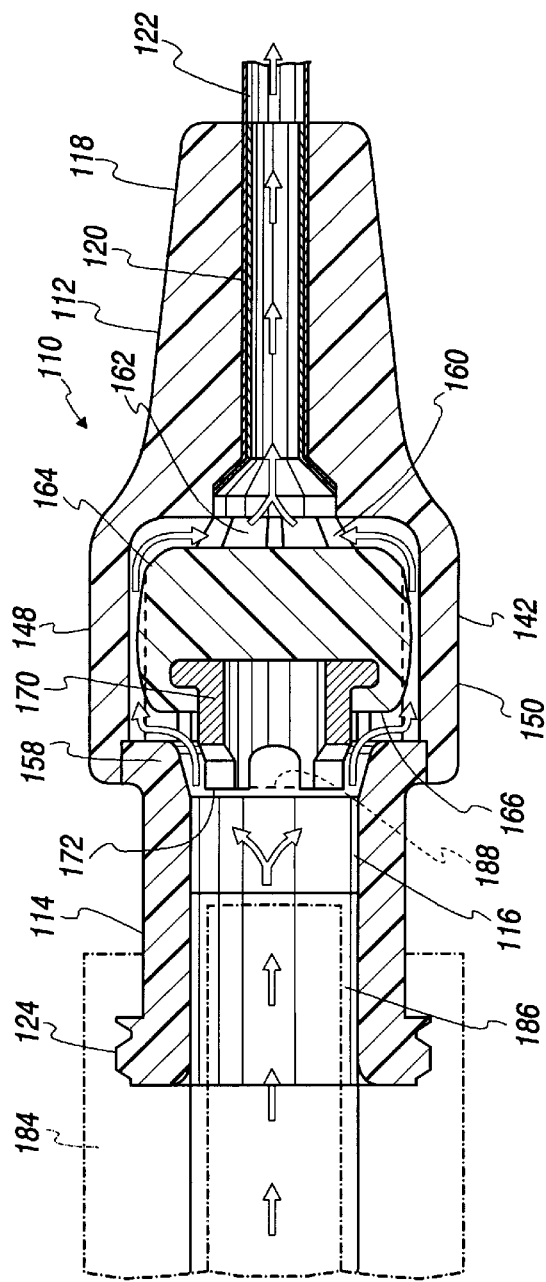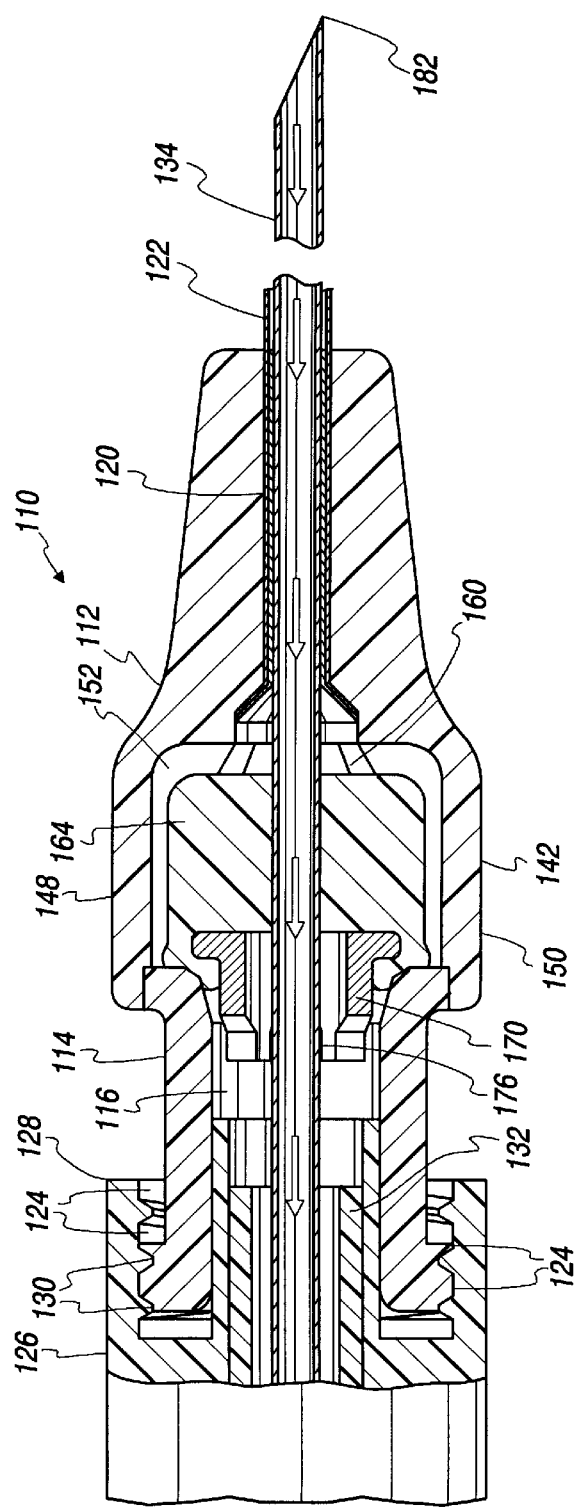

CATHETER HUBS HAVING A VALVE

This application is a continuation-in-part of Ser. No. 08/780,203, filed on Jan. 8, 1997 now abandoned.

BACKGROUND OF THE INVENTION

The present invention relates to a catheter hub. More specifically, the invention is directed to a catheter hub having a valve to regulate fluid flow through the catheter hub.

A previous type catheter hub with valve is disclosed in U.S. Pat. No. 5,085,645 to Purdy et al. The device of this patent includes an elongate resilient valve having a large internal cavity. Being elongate, its length is greater than its width. Such an elongate valve is unstable and tends to deflect or travel in a non-linear manner during use, thus creating an unreliable seal, possibly resulting in leakage. Valve leakage can create significant discomfort for the patient and increased risk of infection, along with increased risk of exposure to blood borne pathogens for healthcare workers.

The internal cavity of the prior art device has a tendency to collapse during use as a result of the blood pressure of the patient. This could unseat the valve and produce leakage. Also, the internal cavity results in significant "dead" space in the flow path, in which blood or liquid can get trapped. Such trapped fluids can pose a risk off infection and/or thrombosis to the patient. In addition to the above, an elongate valve results in a longer catheter, which is harder for healthcare workers to use while being more expensive to fabricate.

SUMMARY OF THE INVENTION

The present invention is directed to a catheter hub including a housing having a connection end defining a first fluid passageway and a catheter end defining a second fluid passageway. The housing includes a plurality of hub walls arranged in a geometric configuration. The hub walls define a valve chamber. The catheter hub further includes a valve positioned in the valve chamber for regulating fluid flow through the chamber between the first and second fluid passageways. The catheter hub further includes an actuator for actuating the valve.

The primary object of the present invention is to provide a catheter hub that includes an internal valve for regulating fluid flow through the catheter hub.

An important object of the present invention is to provide a catheter hub having a unique housing including a plurality of hub walls arranged in a geometric configuration that allows for the easy use and handling of the catheter hub.

Another important object of the present invention is to provide a catheter hub having an actuator that cooperates with a standard luer fitting to actuate the valve.

Still another object of the present invention is to provide a catheter hub with a valve that provides a reliable seal.

A further object at the present invention is to provide a catheter hub without a "dead" space, to improve flushability.

Other objects and advantages of the present invention will become apparent to those skilled in the art upon a review of the following detailed description of the preferred embodiments and the accompanying drawings.

BRIEF DESCRIPTION OF THE DRAWINGS

FIG. 3 is a cross-sectional view taken through the center of the catheter hub according to the present invention with the valve in a closed position;

FIG. 3A is a cross-sectional view taken along line 3A—3A of FIG. 3;

FIG. 4 is a view similar to the view of FIG. 3 showing the valve in an open position;

FIG. 5 is a cross-sectional view of the catheter hub according to the present invention attached to the first end of the needle protector with the needle extending from the needle protector through the catheter hub;

DETAILED DESCRIPTION OF THE PREFERRED EMBODIMENTS

Figure 1:
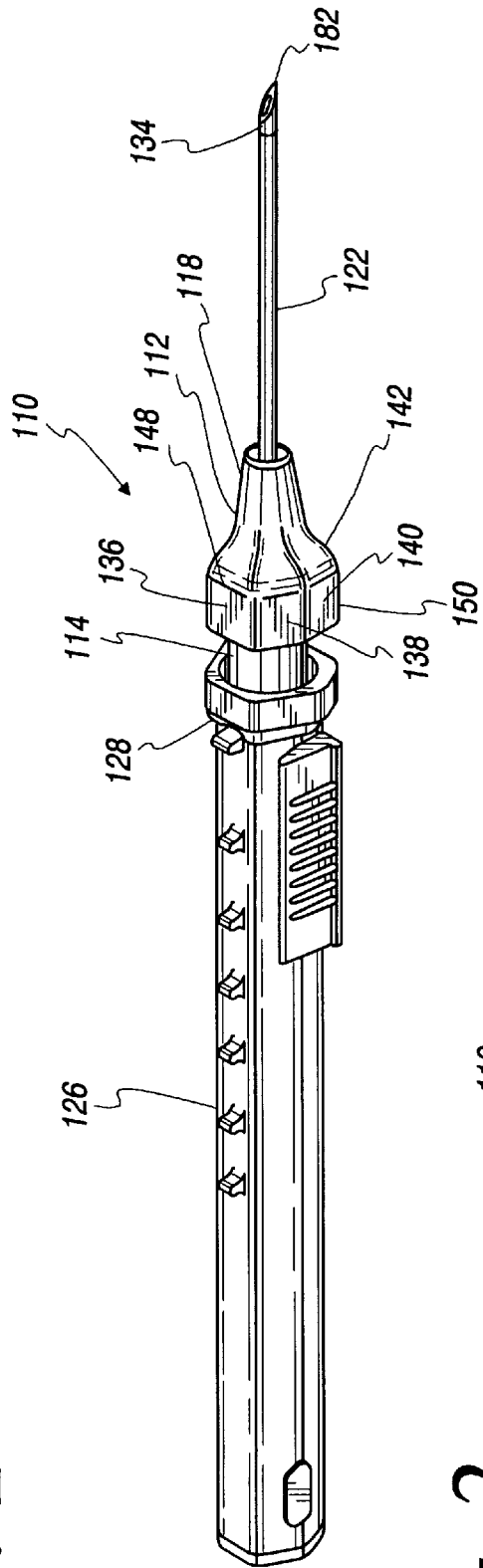
FIG. 1 is a perspective view showing the catheter hub according to the present invention positioned on the end of a needle protector.

The preferred embodiments and best mode of the present invention will now be described in detail with reference being made to the drawings. The catheter hub of the present invention is indicated generally in the drawings by the reference number "110".

Referring to FIGS. 1 and 3, the catheter hub 110 includes a housing 112 having a connection end 114 defining a first fluid passageway 116 and a catheter end 118 defining a second fluid passageway 120. As shown in FIG. 3, the catheter end 118 includes a catheter 122 consisting of a polymeric material positioned in the second fluid passageway 120. The connection end 114 includes a plurality of threads 124. The connection end 114 and the threads 124 are usually constructed to conform with American National Standard Institute No. ANSI/HIMA MD70. 1—1983 relating to luer lock fittings, which is incorporated herein by reference.

Referring to FIGS. 1 and 5, the catheter hub 110 can be attached to, for example, a needle protector 126 having a first end 128. The first end 128 includes a plurality of threads 130 that mates with the plurality of threads 124 of the housing 112. The needle protector 126 includes a needle protector projection 132 that extends into the first fluid passageway 116. The first end 128 and the threads 130 of the needle protector 126 are usually constructed to conform with American National Standard Institute No. ANSI/HIMA MD70. 1—1983. The needle protector 126 includes a needle 134 that extends through the catheter hub 110. It should be understood that the catheter hub 110 can be used with a variety of catheter insertion devices with the needle protector 126 being one example of such a device.

Referring to FIGS. 3 and 3A, the housing 112 includes a plurality of hub walls arranged in a geometric configuration. In the preferred embodiment, as shown in FIG. 3A, the housing 112 includes a first hub wall 136, a second hub wall 138, a third hub wall 140, a fourth hub wall 142, a fifth hub wall 144 and a sixth hub wall 146. As shown in FIGS. 3 and 3A, the housing 112 includes a top 148 and a bottom 150. The fourth hub wall 142 is positioned at the bottom 150 of the housing 112. When so positioned, the fourth hub wall 142 is planar. The planar surface provided by the fourth hub wall 142 provides a flat, smooth surface that can rest against the skin of a patient during use of the catheter hub 110. As described below, this allows the catheter hub 110 to be easily positioned at the site of the blood vessel into which the catheter 122 is to be inserted. As shown in FIG. 3A, the geometric configuration formed by the hub walls 136–146 is a hexagon. However, it should be understood that a variety of polygonal configurations can be used as long as there is a planar surface adjacent the bottom 148 of the housing 112.

Still referring to FIGS. 3 and 3A, the hub walls 136–146 define a valve chamber 152 having a shoulder end 154 and a passageway end 156. As shown in FIG. 3, the connection end 114 of the housing 112 defines an annular shoulder 158 adjacent the shoulder end 154 of the valve chamber 152. As shown in FIG. 3A, the housing 112 defines a plurality of inwardly extending valve ribs 159 in the valve chamber 152. A valve seat 160 is positioned in the valve chamber 152 adjacent the passageway end 156. The valve seat 160 defines a plurality of fluid openings 162 that allows for fluid flow between the second fluid passageway 120 of the catheter end 118 of the housing 112 and the valve chamber 152.

As shown in FIGS. 3 and 3A, the catheter hub 110 includes a valve 164 positioned in the valve chamber 152. The valve 164 is comprised of a resilient material having a substantially cylindrical configuration. As shown in FIG. 3, the valve 164 has an actuator end 166 and a housing end 168. When the valve 164 is in its normally closed position, as shown in FIG. 3, the actuator end 166 is engaged with the annular shoulder 158 of the connection end 114. This engagement acts to seal the valve chamber 152 from the first fluid passageway 116 of the connection end 114 of the housing 112. The housing end 168 of the valve 164 engages the valve seat 160. The valve 164 can consist of a variety of resilient materials, with rubber, silicon and polyisoprene being preferred.

In the embodiment illustrated in FIGS. 3 and 3A, the valve 164 is preferably a short plug-type valve where the diameter is greater than the length. The diameter is preferably about 0.230 +0.003 inches. The present valve 164 is made of solid material and does not have an internal cavity, thereby providing a highly flushable valve that eliminates the risk of fluid stagnation and subsequent infection. The present valve 164 can float within a certain radial tolerance and still make a positive seal. Thus, alignment of the valve 164 is not critical in that it simply drops into the chamber formed by the housing 112 and the connection end 114. Sealing is accomplished between the valve 164 and the annular shoulder 158, which both have fairly large areas of contact. In addition to the above, the short plug-type valve 164 permits the catheter to be made shorter in length, thus improving insertion and reducing the expense of manufacture.

Referring to FIG. 3, the catheter hub 110 includes an actuator 170 that is positioned in the first fluid passageway 116. The actuator 170 includes a luer end 172 and a valve end 174. The actuator 170 is free to move within the first fluid passageway 116 and the valve chamber 152. The actuator 170 defines a needle passageway 176 that extends longitudinally between the luer and valve ends 172 and 174. As shown in FIG. 3, the valve end 174 of the actuator 170 includes an annular flange 178 that is received by a recess 180 defined by the valve 164 at the actuator end 166. This allows a portion of the valve 164 to be positioned between the annular shoulder 158 and the annular flange 178. The annular flange 178 provides structural support for the valve 164 at the actuator end 166 so that a superior seal is formed.

Referring to FIGS. 1–5, the operation and intended use of the catheter hub 110 will be described. As shown in FIGS. 1 and 5, the catheter hub 110 is attached to the needle protector 126 by insertion of the projection 132 into the first fluid passageway 116 and the mating of the threads 124 and 130. The projection 132 is adapted so that it does not move the actuator 170 to actuate the valve 164 regardless of the travel of the projection into the first fluid passageway 116. As shown in FIGS. 1 and 5, the needle 134 of the needle protector 126 extends through the projection 132, into the needle passageway 176 of the actuator 170, the valve 164, the valve seat 160, the catheter 122 to the exterior of the catheter hub 110. When so positioned, the pointed end 182 of the needle 134 can be inserted in the blood vessel of the patient.

During use of the catheter hub 110, the fourth wall 142 of the housing 112, which provides a planar surface, is positioned on the skin of the patient adjacent the injection site. This allows the catheter hub 110 and the needle 126 to be moved easily along the skin during insertion of the needle 134 into the blood vessel. When the blood vessel is pierced, blood "flashes" or moves through the hollow needle 134 as indicated by the arrows in FIG. 5. The blood enters the needle protector 126 where it is vented. The needle 134 guides the catheter 122 into the blood vessel. After insertion of the catheter 122 into the blood vessel, the needle 134 is retracted into the needle protector 126. This results in the needle 134 being retracted from the second fluid passageway 120, the valve seat 160, the valve 164, the actuator 170 and the first fluid passageway 116. After retraction of the needle 134, the catheter hub 110 is detached from the needle protector 126.

As shown in FIG. 3, blood moving in the direction indicated by the arrows through the second fluid passageway 120, the valve seat 160 and the valve chamber 152 is prevented from entering the first fluid passageway 116 due to the seal created between the valve 164 and the annular shoulder 158. This prevents leakage of blood to the exterior of the catheter hub 110.

Figure 2:
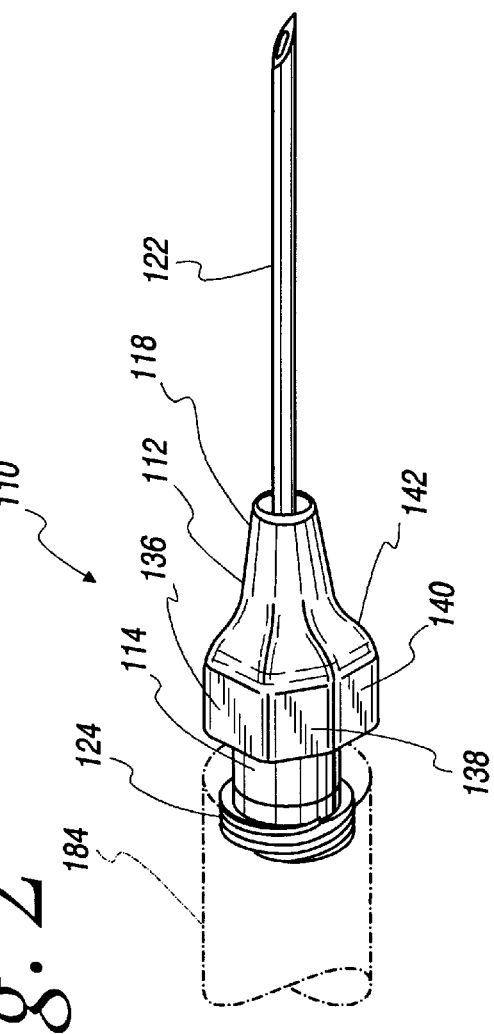
FIG. 2 is a perspective view of the catheter hub according to the present invention connected to a standard luer fitting.

Referring to FIGS. 2, 3 and 4, a conventional luer 184, conforming with American National Standard Institute No. ANSI/HIMA MD70.1—1983 relating to luer lock fittings, can be attached to the connection end 118 of the housing 112. The luer 184 is in communication with, for example, intravenous tubing that is connected to a supply of intravenous fluid (not shown). It should be understood that a variety of devices can be attached to the connection end 114 depending on the application.

Referring to FIGS. 3 and 4, the luer 184 includes a luer projection 186 that extends into the first fluid passageway 116 of the housing 112. The luer projection 186 includes an actuator surface 188 that engages the luer end 172 of the actuator 170. Movement of the luer 184 results in corresponding movement of the actuator 170. This movement causes the actuator 170 to move the valve 164 from the closed position as shown in FIG. 3 to the open position as shown in FIG. 4. As previously described, the valve 164 is comprised of a resilient material. Therefore, the valve can be compressed, as shown in FIG. 4, to allow the actuator end 166 of the valve 164 to become disengaged from the annular shoulder 158. Intravenous fluid is allowed to flow in the direction indicated by the arrows in FIG. 4 when the valve 164 is in the open position. This allows the intravenous fluid in communication with the luer 184 to pass through the catheter hub 110 into the blood vessel of the patient. It should also be understood that blood or some other bodily fluid can be drawn from the patient through the catheter hub 110 with the valve 164 controlling the flow of the fluid between the first and second fluid passageways 116 and 120, respectively. When the luer 184 is moved away from the actuator 170, the actuator end 166 of the valve 164 engages the annular shoulder 156 to reseal the valve chamber 152 as shown in FIG. 3.

Figure 6:
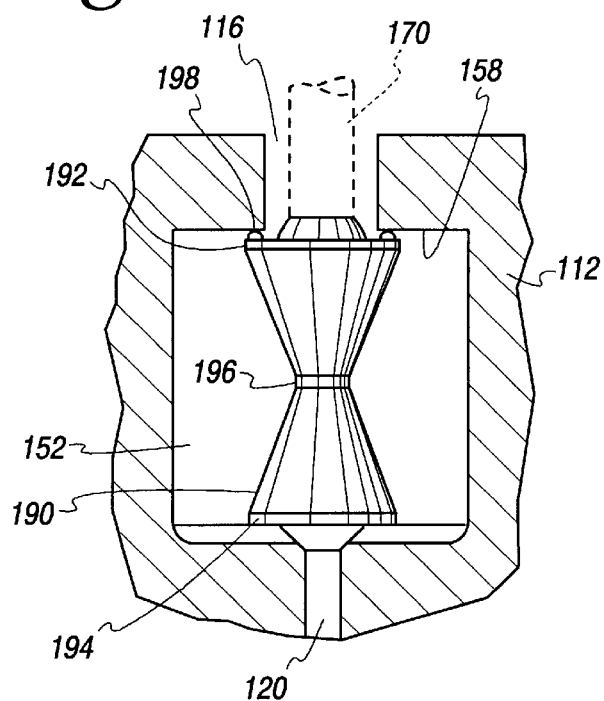
FIG. 6 is a schematic view showing a second embodiment valve in a closed position.
Figure 7:
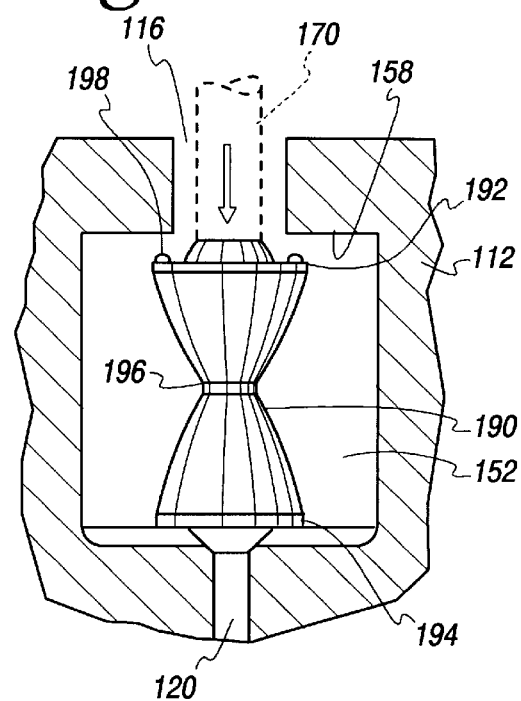
FIG. 7 is a view similar to the view of FIG. 6 showing the valve in an open position.

A second embodiment valve is shown in FIGS. 6 and 7. In this embodiment, the valve 190 is comprised of a resilient material having a substantially cylindrical configuration with an "hour glass" shape. The valve 190 includes an actuator end 192 positioned adjacent the annular shoulder 158 of the housing 112 and an opposed housing end 194 positioned adjacent the passageway end 156 of the valve chamber 152. A center portion 196 is positioned between the actuator and housing ends 192 and 194. The center portion 196 has a smaller diameter than the actuator and housing ends 192 and 194 to provide the valve 190 with the hour glass shape. An annular seal 198 is positioned on the actuator end 192. The annular seal 198 engages the annular shoulder 158 to provide a seal between the valve chamber 152 and the first fluid passageway 116. The second embodiment valve 190 is shown in its normally closed position in FIG. 6. An actuator 170 is moved in the direction indicated by the arrow to compress the valve 190. This results in the actuator end 192 and the annular seal 198 being moved away from the annular shoulder 158 to break the seal between the first fluid passageway 116 and the valve chamber 152. It has been found that the narrow center portion 196 allows for greater flexibility of the valve 190 during compression.

Figure 8:
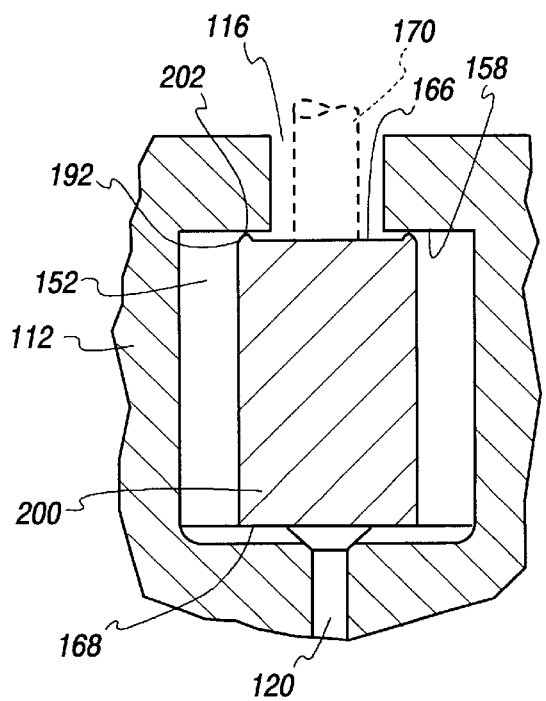
FIG. 8 is a schematic view showing a third embodiment valve in a closed position.
Figure 9:
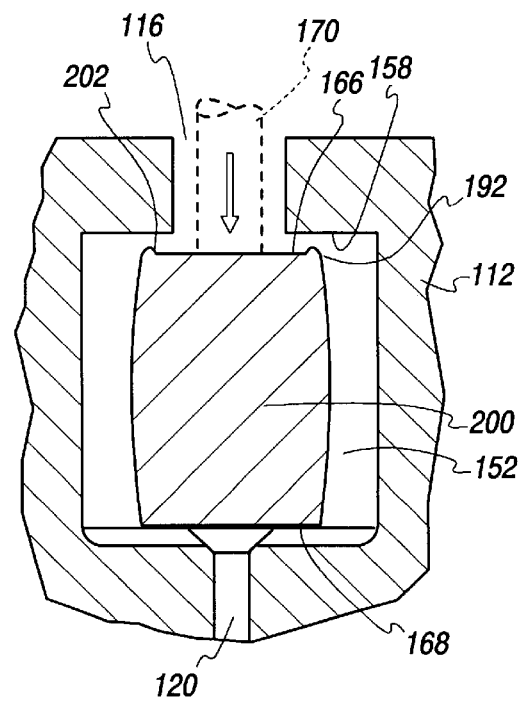
FIG. 9 is a view similar to the view of FIG. 8 showing the valve in an open position.

Referring to FIGS. 8 and 9, a third embodiment valve is shown. In this embodiment, the valve 200 is substantially the same as the above described first embodiment valve 170. The valve 200 includes an integral annular seal 202 adjacent the actuator end 192 of the valve. As shown in FIG. 8, the annular seal 202 engages the annular shoulder 158 in its normally closed position to provide a seal between the first fluid passageway 116 and the valve chamber 152. As shown in FIG. 9, an actuator 170 engages the actuator end 166 of the valve 200 to cause the valve to become compressed. This results in the annular seal 202 becoming disengaged from the annular shoulder 158 to break the seal between the annular seal and the annular shoulder. This allows for fluid flow from the first fluid passageway 116 into the valve chamber 152.

Figure 10:
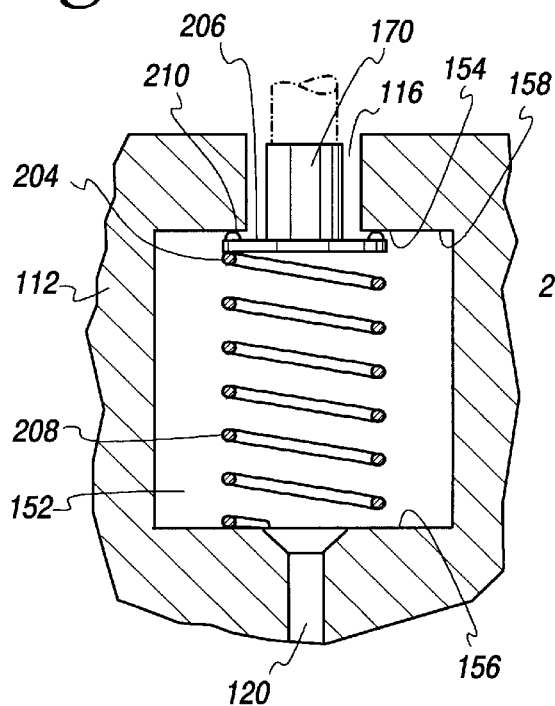
FIG. 10 is a schematic view showing a fourth embodiment valve in a closed position.
Figure 11:
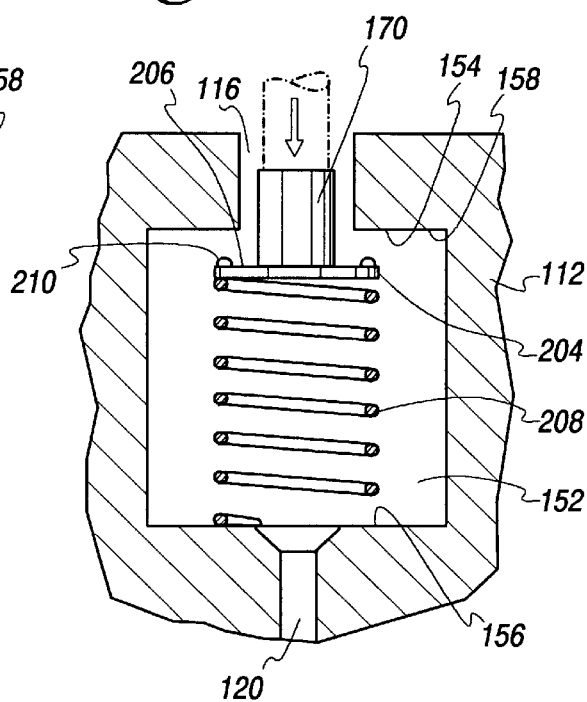
FIG. 11 is a view similar to the view of FIG. 10 showing the valve in an open position.

Referring to FIGS. 10 and 11, a fourth embodiment valve is shown. In this embodiment, the valve 204 includes a valve plate 206 adjacent the shoulder end 154 of the valve chamber 152 and a coiled spring 208 positioned between the valve plate 206 and the passageway end 156 of the valve chamber 152. An annular seal 210 is positioned on the valve plate 206 to provide a seal between the valve plate and the annular shoulder 158. This seal prevents the fluid flow between the first fluid passageway 116 and the valve chamber 152. The valve plate 206 is biased by the coiled spring 208. The valve 204 is shown in its normally closed position in FIG. 10. Referring to FIG. 11, movement of the actuator 170 in the direction indicated by the arrow causes the coiled spring 208 to become compressed thereby allowing movement of the valve plate 206 and the annular seal 210 away from the annular shoulder 158. This allows for fluid flow between the first fluid passageway 116 and the valve chamber 152.

Figure 12:
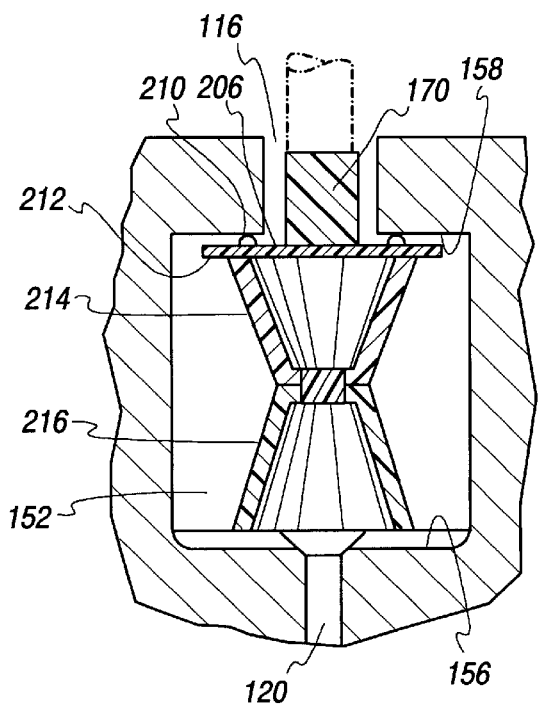
FIG. 12 is a schematic view showing a fifth embodiment valve in a closed position.
Figure 13:
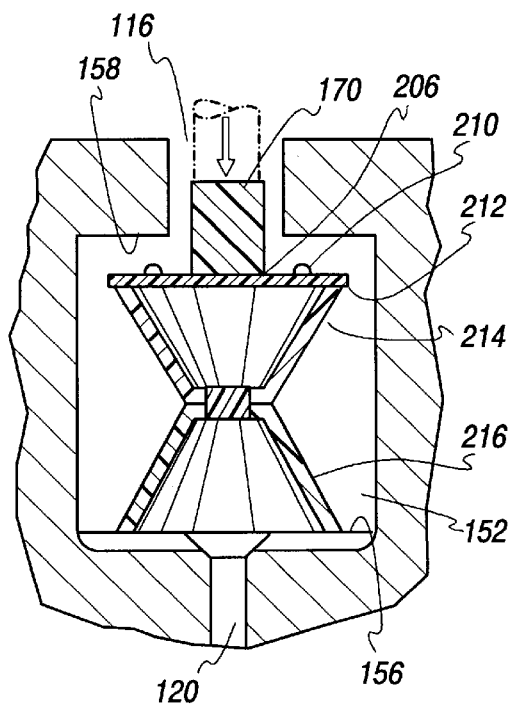
FIG. 13 is a view similar to the view of FIG. 12 showing the valve in an open position.

Referring to FIGS. 12 and 13, a fifth embodiment valve is shown. In this embodiment, the valve 212 is substantially the same as the fourth embodiment valve 204. However, the valve 212 includes two opposed Bellville springs 214 and 216 positioned between the valve plate 206 and the passageway end 156 of the valve chamber 152. The valve 212 is shown in a closed position in FIG. 12. As shown in FIG. 13, the valve 212 is opened by movement of the actuator 170 in the direction indicated by the arrow. This movement causes the springs 214 and 126 to compress thereby allowing the valve plate 206 and annular seal 210 to move away from the annular shoulder 158. This allows fluid flow from the first fluid passageway 116 into the valve chamber 152.

Figure 14:
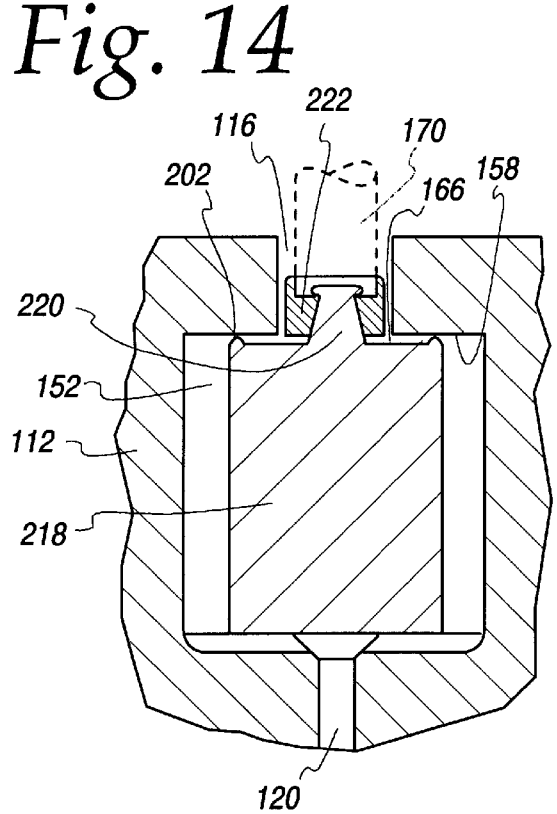
FIG. 14 is a schematic view showing a sixth embodiment valve in a closed position.
Figure 15:
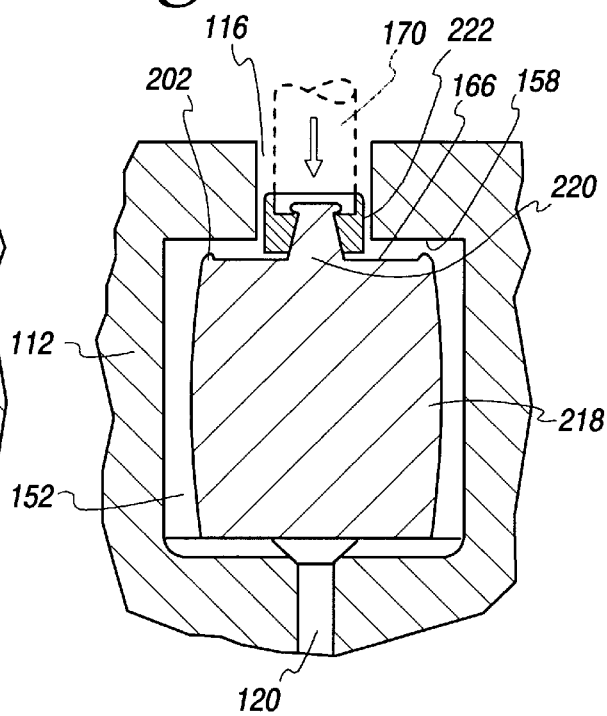
FIG. 15 is a view similar to the view of FIG. 14 showing the valve in an open position.

Referring to FIGS. 14 and 15, a sixth embodiment valve is shown. In this embodiment, the valve 218 is similar to the third embodiment valve 200 shown in FIGS. 8 and 9. The valve 218 includes an actuator projection 220 extending from the actuator end 166 of the valve where it is received by the first fluid passageway 116 of the connection end 114 of the housing 112. The actuator end 166 includes an annular seal 202 that engages the annular shoulder 158 to provide a seal between the first fluid passageway 116 and the valve chamber 152. A retaining flange 222 is positioned on the actuator projection 220. The actuator 170 engages the retaining flange 222. As shown in FIG. 15, movement of the actuator 170 in the direction indicated by the arrow causes the valve 218 to compress thereby allowing the annular seal 202 to become disengaged from the annular shoulder 158. This allows for fluid flow between the first fluid passageway 116 and the valve chamber 152.

Figure 16:
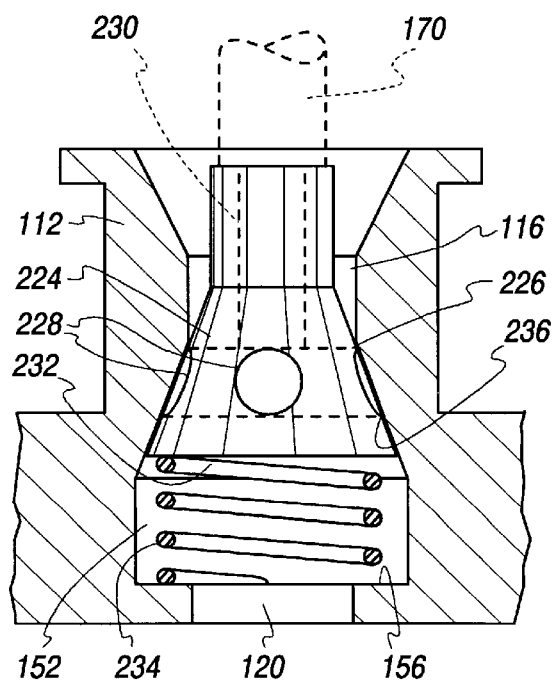
FIG. 16 is a schematic view showing a seventh embodiment valve in a closed position.
Figure 17:
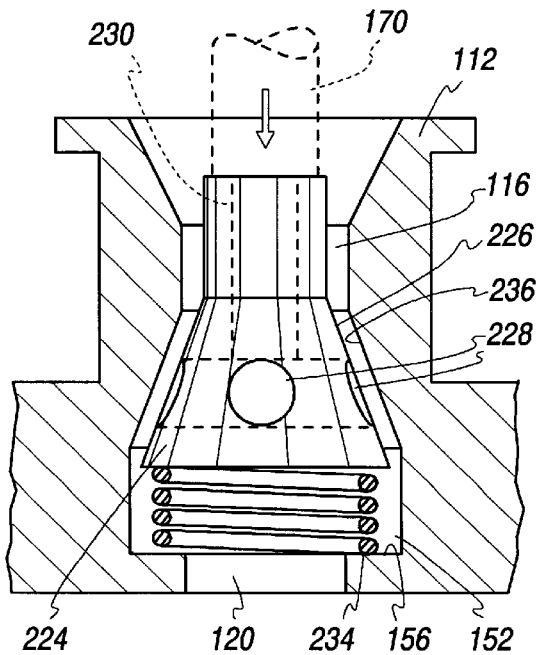
FIG. 17 is a view similar to the view of FIG. 16 showing the valve in an open position.

A seventh embodiment valve 224 is shown in FIGS. 16 and 17. The valve 224 includes a flared wall 226 having a conical configuration. The wall 226 defines a plurality of fluid openings 228 that are in communication with a valve passageway 230. The valve 224 includes a spring wall 232. A coiled spring 234 is positioned between the spring wall 232 and the passageway end 156 of the housing 112 adjacent the second fluid passageway 120.

As shown in FIG. 16, the housing 112 defines an annular shoulder 236 having a flared conical configuration corresponding to the flared wall 226 of the valve 224. When the valve 224 is in its normally closed position, as shown in FIG. 16, the flared wall 226 and the annular shoulder 236 mate to provide a circumferential seal. This seal prevents fluid flow between the first fluid passageway 116 and the valve chamber 152. Referring to FIG. 17, movement of the actuator 170 in the direction indicated by the arrow causes the flared wall 226 to move away from the annular shoulder 236 due to compression of the coiled spring 234 to allow fluid flow through the fluid openings 228 into the valve chamber 152 and the second fluid passageway 120.

Figure 18:
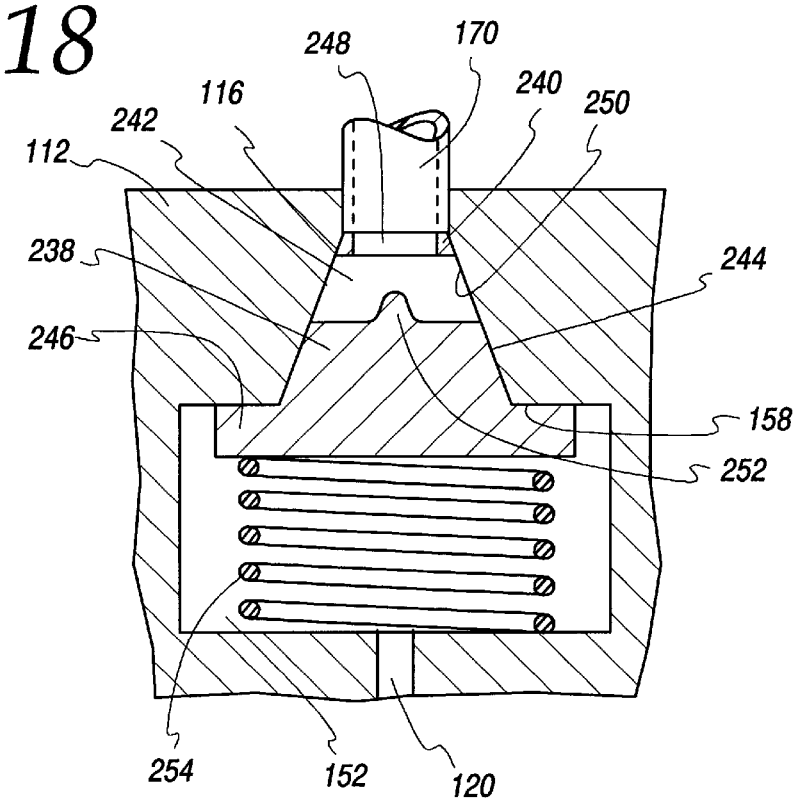
FIG. 18 is a schematic view of an eighth embodiment valve in a closed position.
Figure 19:
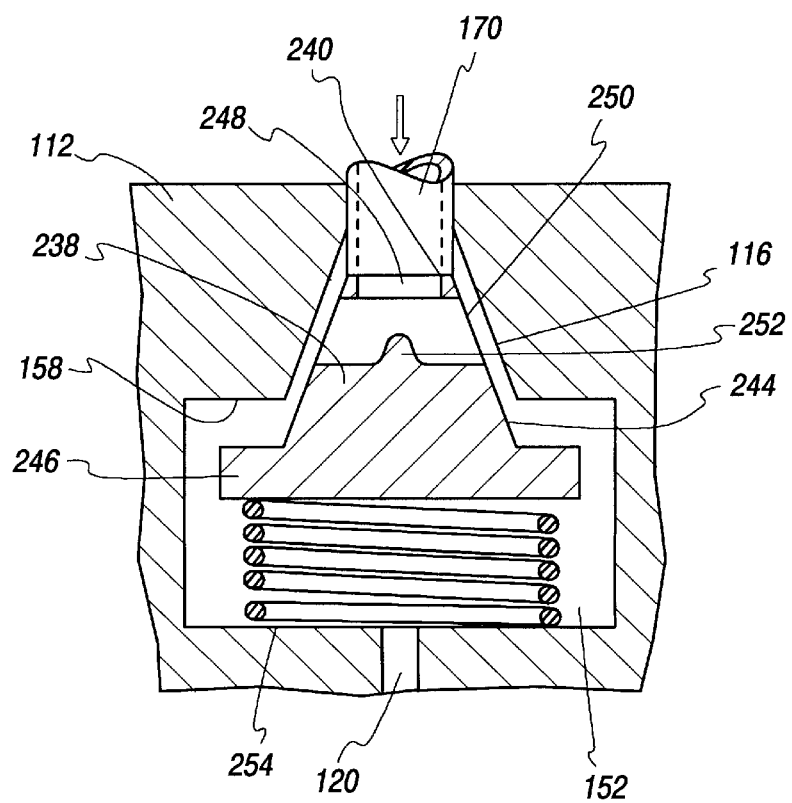
FIG. 19 is a view similar to the view of FIG. 18 showing the valve in an open position.

An eighth embodiment valve is shown in FIGS. 18 and 19. In this embodiment, the valve 238 includes a face interaction portion 240, at least two opposed support legs 242, a flared conically shaped wall 244 and an annular flange portion 246. The portion 240 defines an opening 248 to allow for fluid flow between the actuator 170, such as a luer, and the valve 238. The support legs 242 are positioned at 180° apart. The support legs 242 define at least two opposed leg openings 250 for allowing fluid flow between the opening 248 and the exterior of the valve 238. As shown in FIG. 18, a center baffle 252 is positioned in the valve 238 adjacent the leg openings 250.

Still referring to FIG. 18, the housing 112 defines a first fluid passageway 116 having a flared conical configuration corresponding to the flared wall 244 of the valve 238. When the valve 238 is in its normally closed position, as shown in FIG. 18, the flared wall 244 and the first fluid passageway 116 mate to provide a circumferential seal. The annular flange portion 246 of the valve 238 and the annular shoulder 158 engage one another. When so positioned, the valve 238 provides a seal between the first fluid passageway 116 and the valve chamber 152. A coiled spring 254 forces the valve 238 in the direction of the first fluid passageway 116.

Referring to FIG. 19, movement of the actuator 170 in the direction indicated by the arrow causes the flared wall 244 and the annular flange wall 244 and the annular flange portion 246 to move away from the first fluid passageway 116 and the annular shoulder 158, respectively due to compression of the coiled spring 254. This allows fluid flow through the opening 248, the legs openings 250 into the valve chamber 152. It has been found that the leg openings 250, the baffle 252 and the flared wall 242 increase the rate of fluid flow through the valve 238 and reduce the turbulence or fluid shear of the fluid. The baffle 252 divides or splits the fluid flow into two opposite directions. Once separated, the flow can be smoothly channeled into the flow path. This prevents extra turbulence that may occur when fluid is forced over ribs or through slots, holes or other cut-outs.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

I claim:

1. A catheter hub comprising:
   a housing having a connection end defining a first fluid passageway and a catheter end defining a second fluid passageway, said housing including a plurality of hub walls, with one hub wall forming a bottom of the housing and said bottom being wider than any other said hub wall, said plurality of hub walls defining a valve chamber;
   a valve positioned in said valve chamber for controlling fluid flow in both directions through said chamber between said first and second fluid passageways wherein the valve is a solid member having a diameter larger than length to form a plug-type valve, and
   an actuator means for actuating said valve.

2. The invention of claim 1, wherein said catheter end includes a catheter consisting of a polymeric material.

3. The invention of claim 1, wherein said connection end includes a plurality of threads.

4. The invention of claim 1, wherein said connection end defines an annular shoulder adjacent said valve chamber.

5. The invention of claim 1, wherein said housing includes a top and a bottom, at least one of said hub walls being planar at said bottom.

6. The invention of claim 1, wherein said housing includes a plurality of hub walls arranged in a polygonal configuration.

7. The invention of claim 6, wherein said polygonal configuration is a hexagon.

8. The invention of claim 1, wherein said housing includes a valve seat positioned in said valve chamber adjacent said catheter end.

9. The invention of claim 8, wherein said valve seat includes a plurality of fluid openings to allow for fluid flow between said valve chamber and said second fluid passageway.

10. The invention of claim 1, wherein said valve comprises resilient material, said valve extending substantially between said first and second fluid passageways.

11. The invention of claim 4, wherein said valve comprises resilient material having a substantially cylindrical configuration, said valve having an actuator end and a housing end, said actuator end being engaged with said annular shoulder, whereby actuation of said actuator means causes said actuator end to become disengaged from said shoulder to allow fluid flow through said first fluid passageway, said valve chamber and said second fluid passageway.

12. The invention of claim 11, wherein said actuator end includes an annular seal adjacent said annular shoulder.

13. The invention of claim 11, wherein said actuator end includes an actuator projection received by said first fluid passageway, a retaining flange positioned on said actuator projections, said actuator means engaging said retaining flange.

14. The invention of claim 1, wherein said valve includes an integral annular seal.

15. The invention of claim 1, further including a valve plate and at least one spring positioned within said valve chamber, wherein at least one spring is attached to the valve plate.

16. The invention of claim 14, wherein the valve further includes an actuator projection having a retaining flange, wherein the actuator means engages the retaining flange.

17. The invention of claim 10, wherein the resilient material defines an hourglass shape.

18. The invention of claim 1, wherein the valve is frusto-conical and further includes a spring wall, and the valve chamber further includes a spring positioned adjacent to said spring wall.

19. The invention of claim 1 wherein the valve is frusto-conical and further includes a face interaction portion and a plurality of opposed support legs having a center baffle position and an annular flange portion, wherein each support leg defines a leg opening, and wherein the valve further includes a center baffle positioned adjacent said leg openings in the center baffle position.

* * * * *